(12) United States Patent
Kanai et al.

(10) Patent No.: US 9,576,769 B2
(45) Date of Patent: Feb. 21, 2017

(54) WEAK SIGNAL DETECTION SYSTEM AND ELECTRON MICROSCOPE EQUIPPED WITH SAME

(71) Applicant: Hitachi, Ltd., Chiyoda-ku, Tokyo (JP)

(72) Inventors: Hisaaki Kanai, Tokyo (JP); Wen Li, Tokyo (JP); Masami Makuuchi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/913,029

(22) PCT Filed: Jun. 13, 2014

(86) PCT No.: PCT/JP2014/065668
§ 371 (c)(1),
(2) Date: Feb. 19, 2016

(87) PCT Pub. No.: WO2015/029542
PCT Pub. Date: Mar. 5, 2015

(65) Prior Publication Data
US 2016/0211110 A1 Jul. 21, 2016

(30) Foreign Application Priority Data

Aug. 27, 2013 (JP) .................................. 2013-175142

(51) Int. Cl.
*H01J 37/00* (2006.01)
*H01J 37/22* (2006.01)
(Continued)

(52) U.S. Cl.
CPC ............ *H01J 37/222* (2013.01); *H01J 37/22* (2013.01); *H01J 37/263* (2013.01); *H01J 37/28* (2013.01);
(Continued)

(58) Field of Classification Search
CPC ........ H01J 37/222; H01J 37/263; H01J 37/22; H01J 37/28; H01J 2237/26;
(Continued)

(56) References Cited

U.S. PATENT DOCUMENTS

2008/0215260 A1 9/2008 Kobaru
2009/0226096 A1 9/2009 Namai et al.

FOREIGN PATENT DOCUMENTS

JP 11-224637 A 8/1999
JP 2002-221546 A 8/2002
(Continued)

OTHER PUBLICATIONS

International Search Report (PCT/ISA/210) issued in counterpart International Application No. PCT/JP2014/065668 dated Aug. 5, 2014, with English translation (Four (4) pages).

Primary Examiner — Michael Maskell
(74) Attorney, Agent, or Firm — Crowell & Moring LLP

(57) ABSTRACT

This weak signal detection system has: a statistical data acquisition unit which measures the average value or distribution of an input signal in which is noise superimposed on a desired signal, calculates parameters such as the amplitude or noise dispersion of the desired signal, and outputs the calculated data obtained thereby; a nonlinear characteristic unit which outputs a signal having a nonlinear response with respect to the magnitude of the voltage or the current of the input signal; a signal detection ratio evaluation unit which determines whether the output signal from the nonlinear characteristic unit is the desired signal, calculates the detection ratio in the event that the signal is the desired signal, and outputs detection ratio data; a parameter adjustment unit which, on the basis of detection ratio data obtained by the signal detection ratio evaluation unit and calculated data obtained by the statistical data acquisition unit, adjusts a (Continued)

control parameter pertaining to the responsiveness of the nonlinear characteristic unit; and a signal processing unit which performs signal processing of the output signal of the nonlinear characteristic unit, and conversion to digital data or image data. In so doing, it is possible to provide a weak signal detection system having improved signal detection accuracy, and an electron microscope equipped with the system.

5 Claims, 13 Drawing Sheets

(51) Int. Cl.
    *H01J 37/28*     (2006.01)
    *H01J 37/26*     (2006.01)
    *H01J 37/244*     (2006.01)

(52) U.S. Cl.
    CPC .............. *G01N 2223/418* (2013.01); *G01N 2223/6116* (2013.01); *H01J 37/244* (2013.01); *H01J 2237/221* (2013.01); *H01J 2237/26* (2013.01)

(58) Field of Classification Search
    CPC .............. H01J 2237/221; H01J 37/244; G01N 2223/6116; G01N 2223/418

USPC ................................................ 250/306, 307
    See application file for complete search history.

(56) References Cited

FOREIGN PATENT DOCUMENTS

| | | | |
|---|---|---|---|
| JP | 2002221546 A | * | 8/2002 |
| JP | 2008-186727 A | | 8/2008 |
| JP | 2008-286736 A | | 11/2008 |
| JP | 2009-211960 A | | 9/2009 |

* cited by examiner

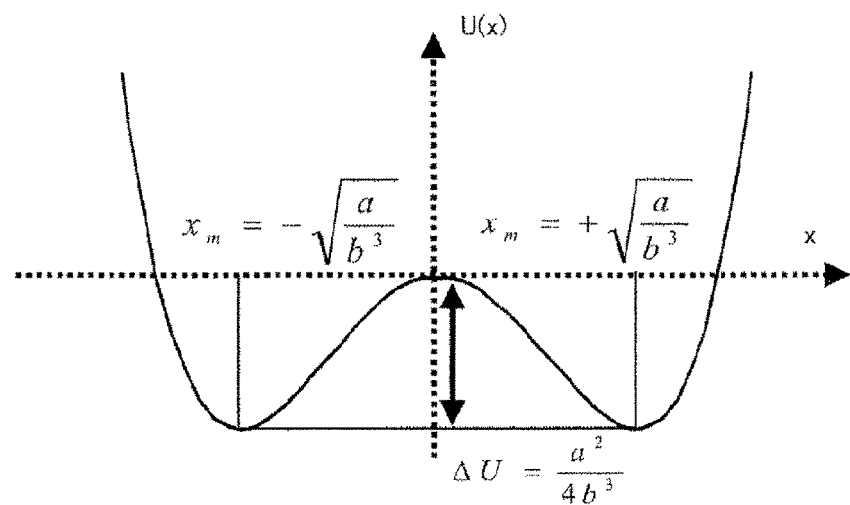
FIG. 14A
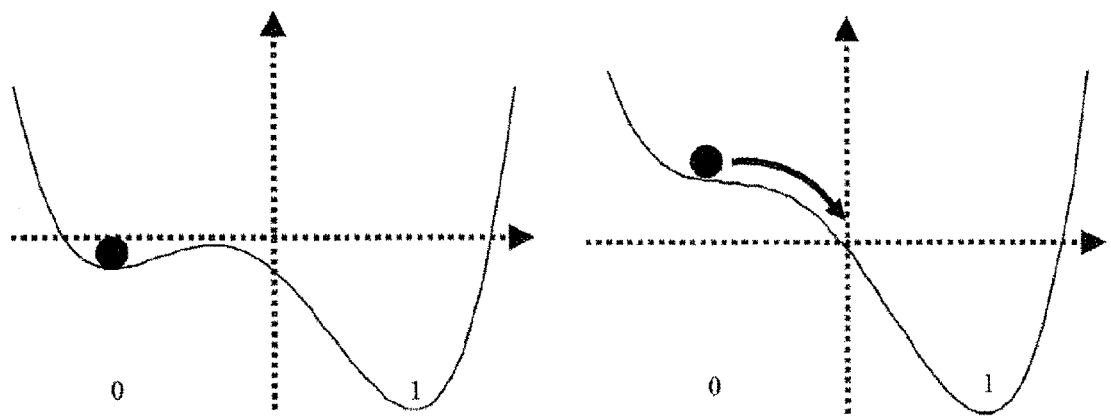
FIG. 14B
FIG. 14C

WEAK SIGNAL DETECTION SYSTEM AND ELECTRON MICROSCOPE EQUIPPED WITH SAME

TECHNICAL FIELD

The present invention relates to a system that detects a weak signal and an electron microscope on which the system is mounted.

BACKGROUND ART

In recent years, in a semiconductor inspection device, medical diagnosis/measurement instrument, or the like, as an inspection object is miniaturized, a signal to noise ratio (Signal to Noise Ratio: SNR) decreases in a detection signal that inspects and measures the object. It is required that a desired signal on which a shape, physicality, and the like of the inspection object are reflected is detected with high accuracy from such a detection signal of a low SNR. For example, a semiconductor inspection/measurement device is a device that irradiates laser, light, an electron beam, or the like onto a wafer being an inspection/measurement object, converts scattered light or a secondary electron from the wafer into an electrical signal by a detector such as photo-multiplier or a scintillator, and inspects and measures shapes of foreign objects or patterns on the wafer through a pre-amplifier, a signal processing circuit, or a display.

In the semiconductor inspection/measurement device, along with the refinement of semiconductors, amount of laser, light, or an electron beam is narrowed down to thereby improve measurement resolving power. On the other hand, by narrowing down the dose, intensity of the desired signal becomes small relatively as compared to noise generated in a detector, an amplifier, or the like, and therefore it is difficult to detect the desired signal with high accuracy.

Therefore, a method is used, for example, by using randomness of noise, averaging detection signals, and detecting the desired signal with high accuracy. JP-A-2008-286736 (Patent Literature 1) describes, for example, "a signal that responds to amplitude of voltage or current of a certain input signal is set to a detection target. In a multi-channel weak signal detection system that detects a plurality of response signals changing in time particularly, an input signal is time-division-multiplexed, conditions of multiplexing are optimized, and averaging-processing in two stages is performed with respect to the response signal, and thereby a weak signal is detected at a high SN ratio".

Further, as a method for improving a signal detection ratio of an input signal with high intensity noise, a technique disclosed in JP-A-2002-221546 (Patent Literature 2) is used. Patent Literature 2 describes "an input signal is input to a nonlinear circuit 11, its output time series is memorized (13), and its power spectrum is calculated (15). Further, noise is generated (16), its intensity is raised gradually, synthesized with the input signal after raising its intensity gradually, and provided to the nonlinear circuit 11. The power spectrum is calculated in each noise intensity, a peak of each power spectrum is detected (18), and its peak value is acquired. Further, a maximum peak value is acquired and used as a period of a weak signal for acquiring the period of the maximum peak (20)".

CITATION LIST

Patent Literature

Patent Literature 1: JP-A-2008-286736
Patent Literature 2: JP-A-2002-221546

SUMMARY OF INVENTION

Technical Problem

According to a method of Patent Literature 1, along with further refinement of semiconductors, it is necessary to further increase the number of times of an averaging operation, and there is a possibility that an increase in a size and cost of the apparatus is caused with along an increase in the number of channels of the detector, or an increase in power consumption is caused by increasing a speed of an signal processing circuit.

Further, according to the method of Patent Literature 2, when the noise intensity is weak and the signal detection ratio decreases as compared to a linear system, noise is superimposed by a noise generation circuit and the noise intensity is optimized, thereby improving the signal detection ratio. However, in this method, noise is superimposed on an input signal in which the noise intensity is weak, and therefore the signal detection ratio may be lower than that obtained in the linear system. For example, when noise is not present in the input signal at all, although an output signal in which the desired signal is completely reproduced is obtained in the linear system, the signal detection rate decreases because noise is superimposed to cause a state transition.

Further, the noise generation circuit that generates noise, the adding circuit that superimposes the generated noise on the input signal, and the like are required, and there is a problem that a circuit scale becomes large and power consumption is increased. In addition, there is a possibility that since noise is generated in the nonlinear signal detection system, the noise wraps around into a peripheral circuit and operations of the system become unstable.

In view of the foregoing, it is an object of the present invention to provide a weak signal detection system that improves signal detection accuracy and an electron microscope on which the system is mounted.

Solution to Problem

To solve the above problem, for example, a configuration described in the scope of claims is adopted.

This application includes a plurality of means to solve the above problem, and one example is a weak signal detection system characterized by including a statistical data acquisition unit that measures an average value or distribution of an input signal in which noise is superimposed on a desired signal, calculates amplitude of the desired signal, noise dispersion, and the like, and outputs obtained calculation data; a nonlinear characteristic unit that outputs a signal that responds nonlinearly to amplitude of voltage or current of the input signal; a signal detection ratio evaluation unit that determines whether an output signal from the nonlinear characteristic unit is the desired signal, calculates a detection ratio assuming the output signal is the desired signal, and outputs detection ratio data; a parameter adjustment unit that adjusts a control parameter pertaining to responsiveness of the nonlinear characteristic unit based on the detection ratio data obtained by the signal detection ratio evaluation unit and the calculation data obtained by the statistical data acquisition unit; and a signal processing unit that performs signal processing of the output signal from the nonlinear characteristic unit and converts the signal-processed output signal into digital data or image data.

Advantageous Effects of Invention

According to the present invention, it is possible to provide the weak signal detection system that improves signal detection accuracy, and the electron microscope on which the system is mounted.

BRIEF DESCRIPTION OF DRAWINGS

FIGS. 14A-14C are diagrams illustrating potential of a bistable nonlinear signal detection system.

DESCRIPTION OF EMBODIMENTS

Figure 1:
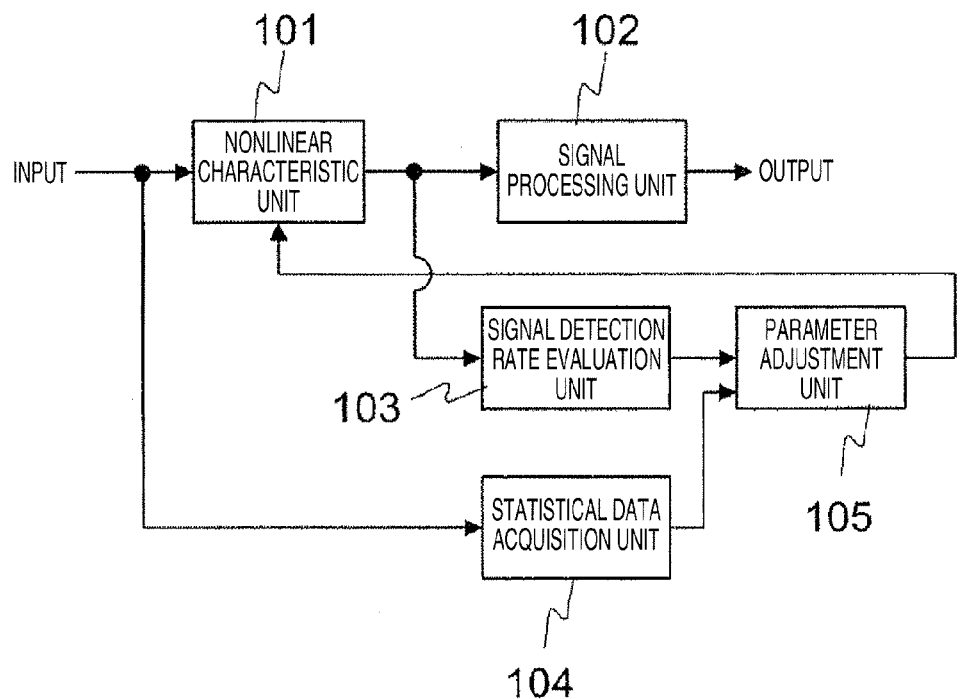
FIG. 1 is a block diagram illustrating a nonlinear signal detection system according to a first embodiment.

Hereinafter, embodiments of the present invention will be described with reference to the attached drawings. In the attached drawings, the same functional elements may be displayed by the same reference numerals. Although the attached drawings illustrate specific embodiments and examples of implementation according to the principle of the present invention, the attached drawings are for understanding the present invention and are not used to restrictively interpret the present invention.

Although the present embodiments describe the present invention in detail enough for those skilled in the art to carry out the present invention, other implementations and modes are also possible, and it needs to be understood that changes in configurations and structures as well as replacements of various elements are possible without departing from the range and the spirit of the technical concept of the present invention.

First Embodiment

FIG. 1 is a diagram illustrating a configuration of a nonlinear signal detection system according to a first embodiment of the present invention. The nonlinear signal detection system of the present invention is configured by statistical data acquisition unit 104 that measures an average value or distribution of an input signal in which noise is superimposed on a desired signal, calculates amplitude of the desired signal, noise dispersion, and the like, and outputs obtained calculation data, nonlinear characteristic unit 101 that outputs a signal that responds nonlinearly to the amplitude of voltage or current of the input signal, signal detection ratio evaluation unit 103 that evaluates a detection ratio of the desired signal in an output signal from nonlinear characteristic unit 101 and outputs detection ratio data, parameter adjustment unit 105 that adjusts control parameter of nonlinear characteristic unit 101 based on the detection ratio data output from signal detection ratio evaluation unit 103 and the calculation data obtained by statistical data acquisition unit 104, and signal processing unit 102 that performs signal processing of the output signal from nonlinear characteristic unit 101 and conversion to digital data or image data.

Nonlinear characteristic unit 101 is characterized in that it includes one or more linear amplifier circuits that linearly amplify an input signal and one or more nonlinear response circuits that respond nonlinearly to the input signal. Further, a gain of the linear amplifier circuit and the nonlinear response circuit is characterized in that it is a parameter for adjusting a state transition level for responding to input signal voltage in the nonlinear characteristic unit.

Statistical data acquisition unit 104 measures the amplitude of the desired signal and noise dispersion in the input signal. In statistical data acquisition unit 104, an example of a method is illustrated for calculating the amplitude of the desired signal and noise dispersion in the case in which the desired signal has binary digital data of Lo and Hi, and the noise is white Gaussian-distribution noise.

Cumulative distribution of the white Gaussian-distribution noise is approximated by a sigmoid function, and therefore voltage value cumulative data in the case in which the white Gaussian-distribution noise is superimposed on the binary desired signal is represented by the following function of [MATH. 1].

$$f(v) = F_L \exp\left(-\frac{(x+v_L)^2}{2\sigma^2}\right) + F_H \exp\left(-\frac{(x-v_H)^2}{2\sigma^2}\right) \quad \text{[MATH. 1]}$$

Here, $F_L$ denotes the frequency of appearance of Lo of the desired signal, $F_H$ denotes the frequency of appearance of Hi of the desired signal, $V_L$ denotes a value of signal voltage of Lo, $V_H$ denotes a value of the signal voltage of Hi, and $\sigma$ denotes a standard deviation of noise. Each parameter is fitted so that a squared error is minimized between the function represented by [MATH. 1] and the obtained accumulated data, thereby calculating the signal amplitude and the noise dispersion.

Signal detection ratio evaluation unit 103 evaluates the detection ratio of the desired signal in the output signal from nonlinear characteristic unit 101 and outputs the detection ratio data. As an example of a method for evaluating the detection ratio of the desired signal, a method is useful for previously using known data rows as the input signal, comparing the known data rows and the output signal from nonlinear characteristic unit 101, and thereby evaluating the signal detection ratio.

Parameter adjustment unit 105 adjusts gains of the linear amplifier circuits and the nonlinear response circuits included in nonlinear characteristic unit 101 based on the calculated data of noise and the signal amplitude calculated by statistical data acquisition unit 104 and the detection ratio data obtained by signal detection ratio evaluation unit 103. As an example of an optimization adjustment method of the gain, a method is used for sweeping each gain, evaluating the signal detection ratio by signal detection ratio evaluation unit 103, and setting each gain to the gain in which the signal detection ratio is maximized.

In addition to the above, a method may be used for previously holding in a memory each gain in which the signal detection ratio is maximized with respect to the signal amplitude and the noise dispersion, reading out an optimal gain from the memory according to values of the signal amplitude and the noise dispersion obtained by statistical data acquisition unit 104, and adjusting nonlinear characteristic unit 101. Signal processing unit 102 performs signal processing of the output signal that is optimized and obtained using the above method by nonlinear characteristic unit 101 and conversion to digital data or image data.

Figure 3:
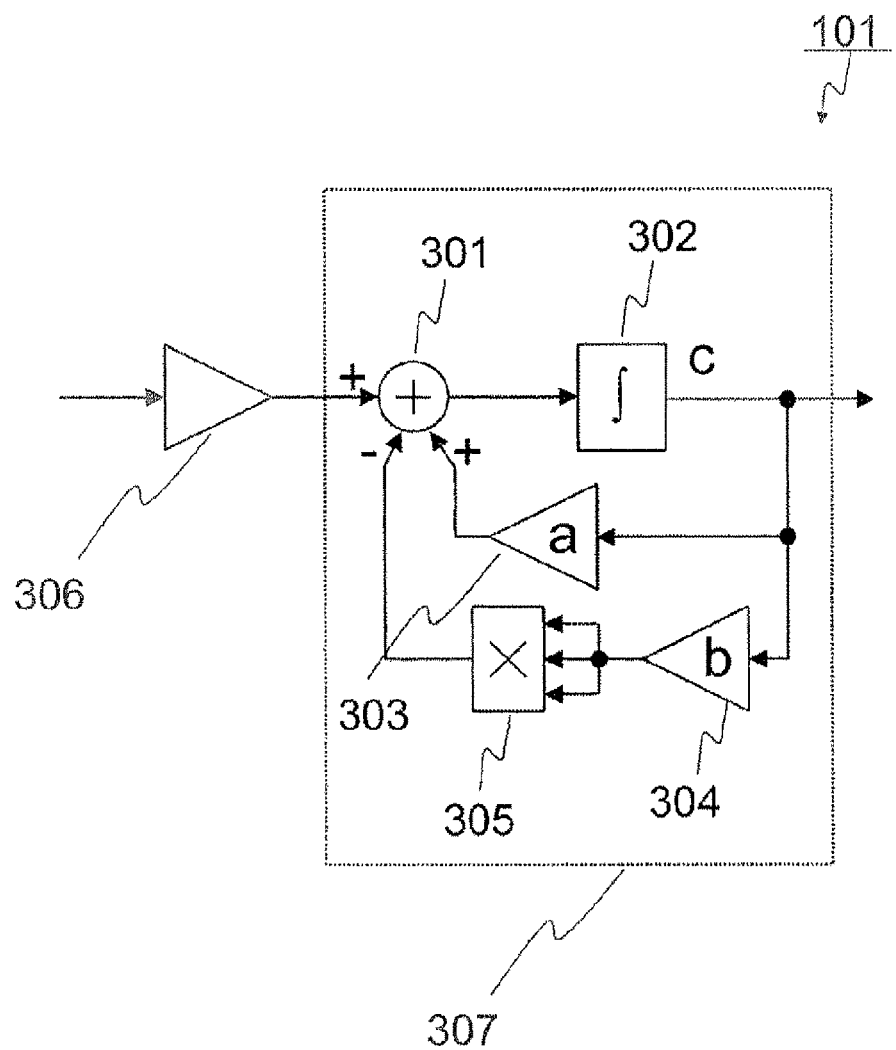
FIG. 3 is a block diagram illustrating an example of a nonlinear characteristic unit configuring the nonlinear signal detection system.

FIG. 3 illustrates an example of a configuration of the nonlinear characteristic unit. First, nonlinear characteristic unit 101 is based on a bistable nonlinear signal detection system represented by [MATH. 2] and [MATH. 3] as a nonlinear signal detection system in which stochastic variation of noise is used and a stochastic resonance phenomenon is used in which an intensity of only the desired signal increases in a weak detection signal of a low SNR.

$$\frac{dx(t)}{dt} = -\frac{dU(t, x)}{dx}$$ [MATH. 2]

$$U(t, x) = -\frac{ax^2}{2} + \frac{b^3 x^4}{4} - s(t)$$ [MATH. 3]

Here, x denotes a position of a particle, U (t, x) denotes potential of a system, s (t) denotes a signal for tilting the potential, t denotes time, and a and b denote constants.

A physical image of the stochastic resonance phenomenon will be described using as an example this bistable nonlinear signal detection system.

FIG. 14 illustrates a potential diagram of the bistable nonlinear signal detection system of [MATH. 3]. As illustrated in FIG. 14(a), first, this potential has two stable states, and there is a barrier having a height of $a^2/4b^3$ between the two states when a signal s (t) is zero. Here, when a particle is assumed to be present in one potential well, the potential is tilted by a weak signal and the particle moves from side to side on a bottom of the potential well as illustrated in FIG. 14(b). When a change in a position of this particle is assumed to be first detectable at the time in which this particle transits to an adjacent well, a change in the position is undetectable in such a weak tilt. When a signal for greatly tilting the potential is further added to this system, there is no barrier that is present between two wells and the particle rapidly transits to another well as illustrated in FIG. 14(c), and a change in the position is detected at this time.

In the case in which a weak signal is set to the desired signal, a large signal is set to noise, and a position of the particle is set to an output signal, when an input signal in which the noise is superimposed on the desired signal is larger than the state transition level represented by [MATH. 4], transition of the output signal occurs.

$$s_0 = \sqrt{\frac{4a^3}{27b^3}}$$ [MATH. 4]

Figure 9:
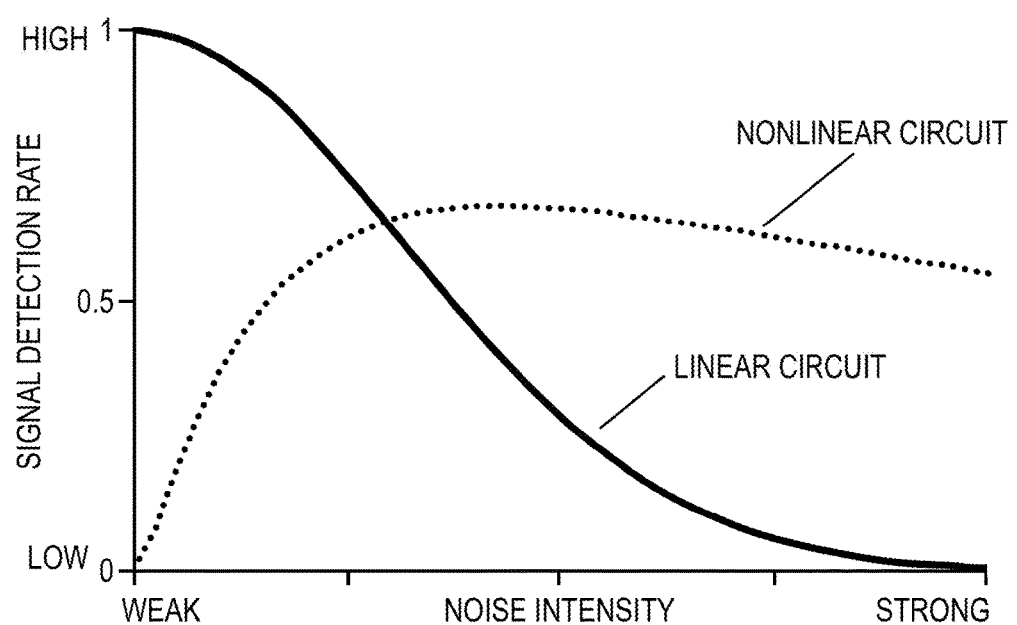
FIG. 9 is a diagram illustrating a signal detection ratio corresponding to noise intensity according to a linear signal detection system and the nonlinear signal detection system.

When the desired signal and noise in which the state transition occurs appropriately are applied, an output signal having a high correlation with the desired signal is detected. FIG. 9 illustrates a signal detection ratio according to the linear system and the nonlinear signal detection system at the time in which intensity of the desired signal is kept constant and noise intensity is set to a parameter. In the linear system, as the noise intensity becomes stronger, the signal detection ratio decreases more. On the other hand, in the nonlinear signal detection system, a higher signal detection ratio is obtained as compared to the linear system in specified noise intensity. In the case in which the noise intensity is weaker than an optimal value, however, the signal detection ratio decreases rapidly and the signal detection ratio decreases greatly as compared to the linear system. The reason is that the input signal matching to removal of the potential barrier is not applied and the state transition is hard to cause.

As illustrated in FIG. 3, nonlinear characteristic unit 101 is configured by linear amplifier circuit 306 and nonlinear response circuit 307. Nonlinear response circuit 307 is configured by adding circuit 301 that adds to the input signal two feedback signals from positive feedback amplifier circuit 303 and cube circuit 305, integral circuit 302 that integrates the added signal, positive feedback amplifier circuit 303 that linearly amplifies the integrated signal and outputs it to adding circuit 301, negative feedback amplifier circuit 304 that linearly amplifies the integrated signal and outputs it to cube circuit 305, and cube circuit 305 that outputs to adding circuit 301 a signal obtained by cubing the linearly amplified signal.

As illustrated in [MATH. 4], the state transition level is proportional to a square root of the cube of a positive feedback gain a of positive feedback amplifier circuit 303, and is inversely proportional to a square root of the cube of a negative feedback gain b of negative feedback amplifier circuit 304. Based on the above, to reduce the state transition level, it is sufficient to just either decrease the positive feedback gain a, or increase the negative feedback gain b. To raise the state transition level, it is sufficient to just either increase the positive feedback gain a, or decrease the negative feedback gain b.

According to the above configuration, for example, in the case in which the noise intensity of the input signal is weak, the state transition fails to occur and the signal detection ratio decreases in the nonlinear characteristic unit, the gains of the linear amplifier circuit and the nonlinear response circuit are adjusted, the state transition level is reduced, and the state transition occurs optimally, thereby improving the signal detection ratio. Suppose, further, that the noise intensity of the input signal is strong, and the state transition occurs excessively and the signal detection ratio decreases in the nonlinear characteristic unit. In this case, the gains of the linear amplifier circuit and the nonlinear response circuit are adjusted, the state transition level is raised, and the state transition occurs optimally, thereby improving the signal detection ratio.

On the other hand, the nonlinear characteristic unit having such a configuration exerts an influence not only on the state transition level but also on the response speed and the output signal amplitude due to the positive feedback gain a and the negative feedback gain b.

Figure 8A:
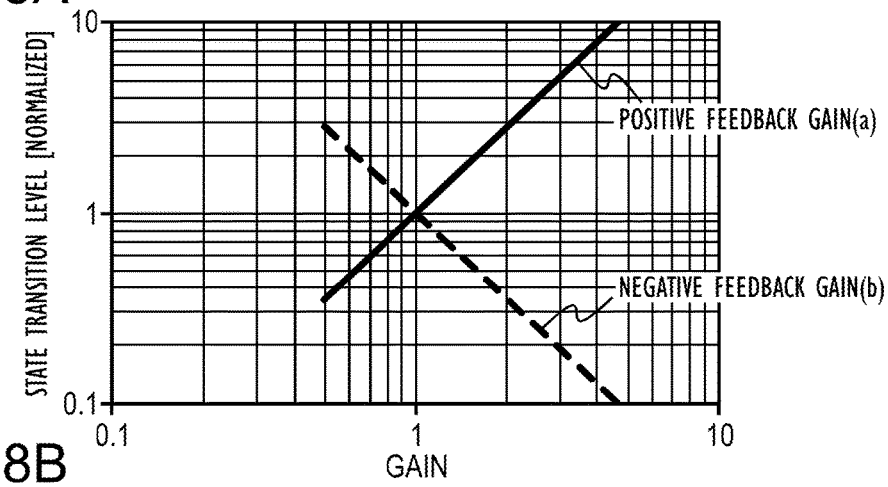
FIGS. 8A-8C are diagrams illustrating an example of sensitivity of the control parameter corresponding to characteristics of the nonlinear characteristic unit.
Figure 8B:
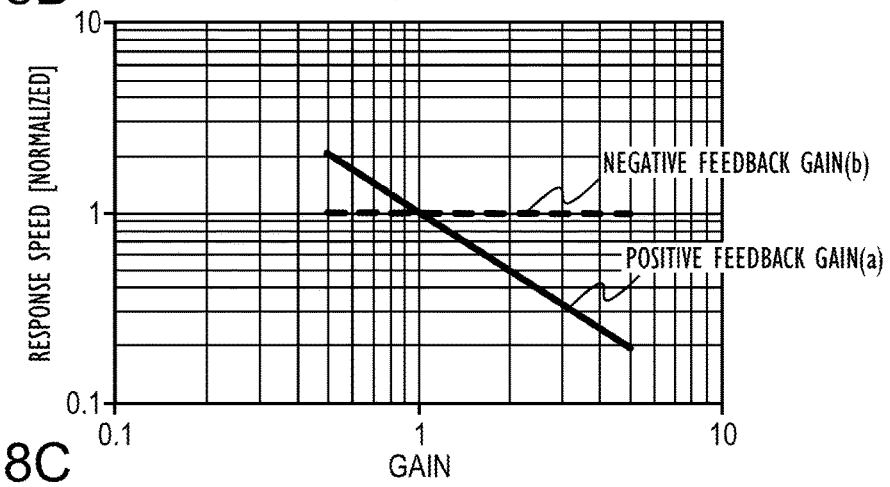
Figure 8C:
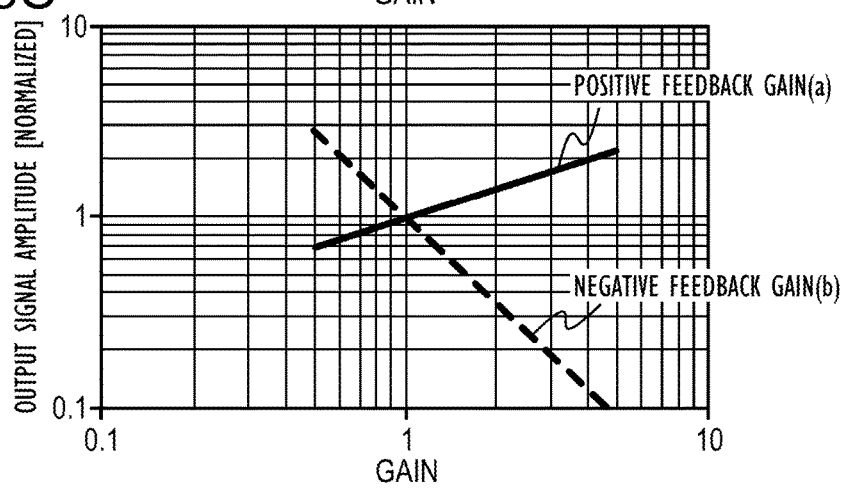

FIG. 8 illustrates sensitivities of the positive feedback gain a and the negative feedback gain b corresponding to the state transition level, the response speed, and the output signal amplitude. As previously described, the state transition level varies in proportion to the square root of the cube of the positive feedback gain, and varies in inverse proportion to the square root of the cube of the negative feedback gain. The response speed varies in inverse proportion to the square root of the positive feedback gain, and the sensitivity corresponding to the negative feedback gain is zero. The output signal amplitude varies in proportion to the square root of the positive feedback gain and varies in inverse proportion to the square root of the cube of the negative feedback gain.

That is, the positive feedback gain a exerts an influence on all characteristics and the negative feedback gain b exerts an influence on the state transition level and the output signal amplitude, and therefore it is impossible to independently set the state transition level, the response speed, and the output signal amplitude. Therefore, priority is determined that any characteristic is optimized, and it is necessary to adjust the positive feedback gain and the negative feedback gain.

Figure 6:
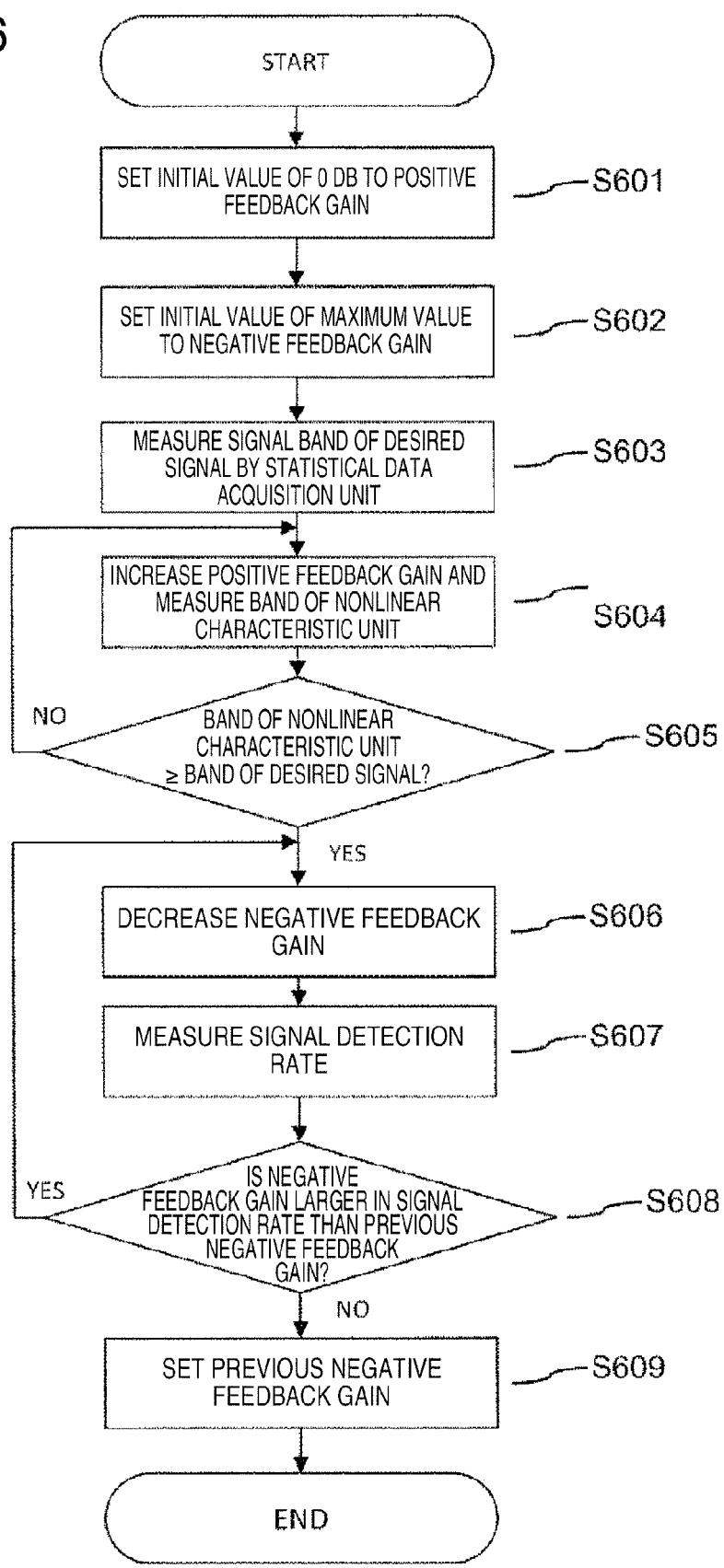
FIG. 6 is a diagram illustrating an example of a flowchart for adjusting a control parameter of the first embodiment.

The adjustment sequence for optimizing the state transition level and the response speed having high priority is illustrated in FIG. 6. When the adjustment sequence is started, the positive feedback gain is first set to 0 dB (S601) and the negative feedback gain is set to a maximum value (S602). The reason is that there is a possibility that in the case in which the positive feedback gain is high, the whole nonlinear characteristic unit switches to a positive feedback operation and the operation becomes unstable. If a stable operation is guaranteed, an initial value is not limited to the above value.

Next, a signal band of the desired signal is measured by statistical data acquisition unit 104 (S603). Next, in order that a band of nonlinear characteristic unit 101 may be made to be higher than that of the desired signal, the positive feedback gain is increased and the band of nonlinear characteristic unit 101 is evaluated (S604). Further, if the band of nonlinear characteristic unit 101 is higher than that of the desired signal, the process proceeds to the next step, and if the band of nonlinear characteristic unit 101 is lower than that of the desired signal, the positive feedback gain is increased again and the band is evaluated (S605).

Next, the negative feedback gain is decreased (S606). The above is equivalent to a raise in the state transition level. Next, the signal detection ratio is evaluated (S607), and whether the negative feedback gain is more in the signal detection ratio than the previous negative feedback gain is confirmed (S608). If the negative feedback gain is not more in the signal detection ratio than the previous negative feedback gain, the previous negative feedback gain is set (S609), and the adjustment is ended. If the negative feedback gain is more in the signal detection ratio than the previous negative feedback gain, the negative feedback gain is further decreased. According to the above adjustment method, it is possible to optimize the band and the signal detection ratio of the nonlinear characteristic unit.

Figure 4:
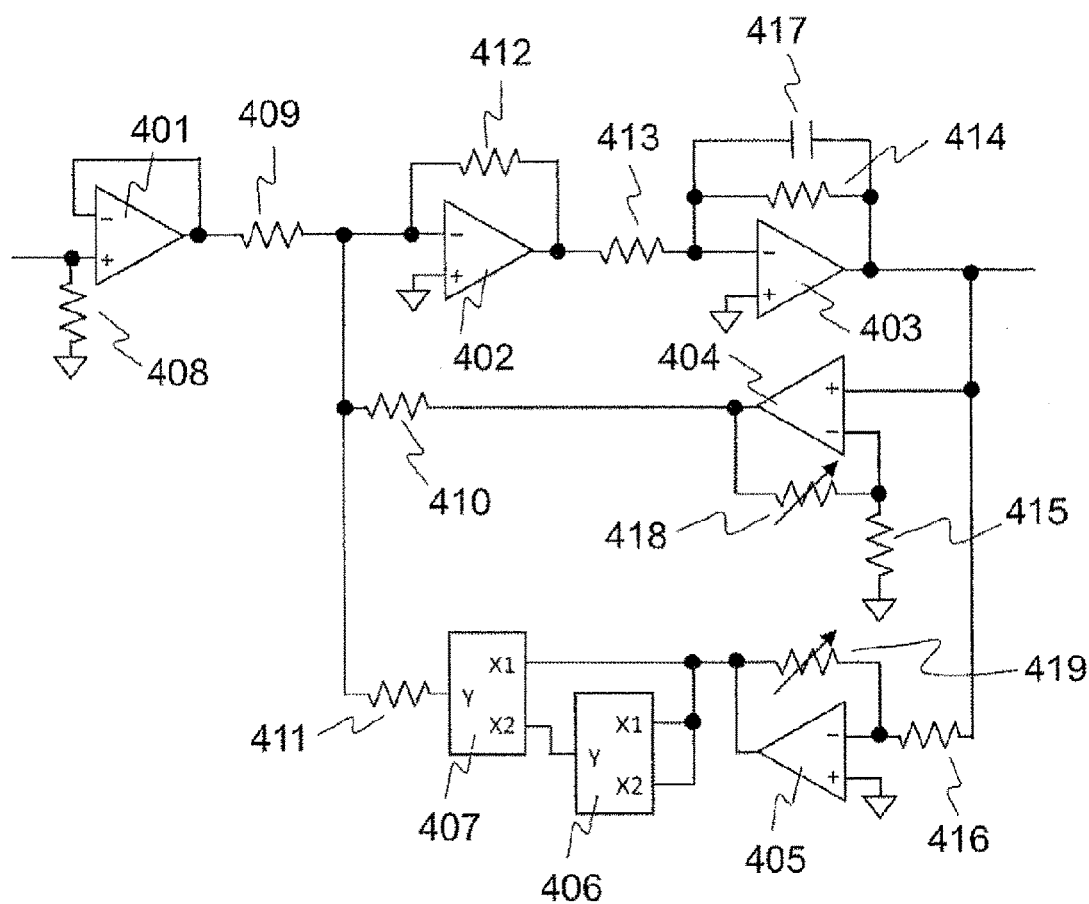
FIG. 4 is a block diagram illustrating an example of a circuit configuration of the nonlinear characteristic unit.

Next, an example of a specific circuit configuration of the nonlinear characteristic unit is illustrated and a method for adjusting the positive feedback gain a and the negative feedback gain b will be described. A specific circuit configuration of the nonlinear characteristic unit illustrated in FIG. 3 is illustrated in FIG. 4. An operational amplifier 401 and a resistance 408 are a pre-linear amplifier circuit (pre-amplifier circuit) for receiving the input signal. The adding circuit is configured by an operational amplifier 402 and resistances 409, 410, 411, and 412, the integral circuit is configured by an operational amplifier 403, resistances 413 and 414, and a capacitor 417, the positive feedback amplifier circuit is configured by an operational amplifier 404, a resistance 415, and a variable resistance 418, the negative feedback amplifier circuit is configured by an operational amplifier 405, a resistance 416, and a variable resistance 419, and the cube circuit is configured by two-input multiplication circuits 406 and 407.

The positive feedback gain a of the positive feedback amplifier circuit can be adjusted by the variable resistance 418, and when a resistance value of the variable resistance 418 is set to Rfa and a resistance value of the resistance 415 is set to Rsa, a gain thereof is represented by (1+Rsa/Rfa). Further, the negative feedback gain b of the negative feedback amplifier circuit can be adjusted by the variable resistance 419, and when a resistance value of the variable resistance 419 is set to Rfb and a resistance value of the resistance 416 is set to Rsb, a gain thereof is represented by −Rsb/Rfb. Here, a configuration is used in which the variable resistances 418 and 419 are varied and the gain is adjusted; further, the resistances 410 and 411 of the adding circuit are also changed into variable resistances, or the gains of the multiplication circuits 406 and 407 are also varied, thereby acquiring the same effect.

According to the above configuration, the positive feedback gain and the negative feedback gain of the nonlinear characteristic unit are adjusted and the state transition level is adjusted to the optimal value. Thereby, in the nonlinear signal detection system, it is possible to improve the SNR of the input signal in a wide noise intensity range. In addition, since a noise generation circuit is not required, it is possible to reduce the system in size, reduce costs, and save power. Further, since the noise generation circuit is not required, stabilization of the system is anticipated.

Figure 5:
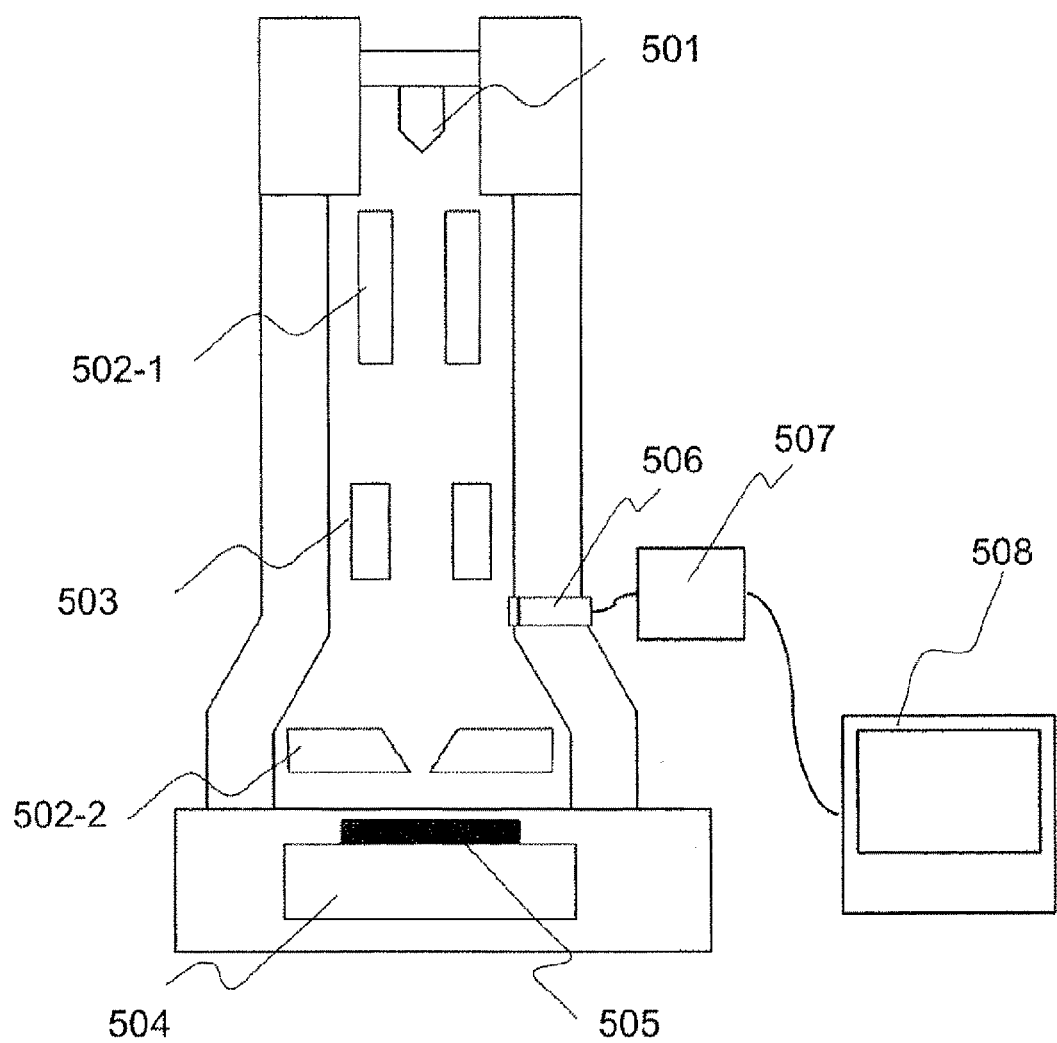
FIG. 5 is a diagram illustrating an example of an apparatus to which the nonlinear signal detection system is applied.

FIG. 5 is a diagram illustrating an example of an apparatus to which the nonlinear signal detection system is applied. An electron microscope is configured by electron gun 501 that emits an electron beam, lenses 502-1 and 502-2 for reducing a diameter of the electron beam, deflection electrode 503 that adjusts an irradiation position of the electron beam, stage 504 for placing sample 505, detector 506 that detects a secondary electron emitted from sample 505, signal processing board 507 that amplifies a detection signal, converts it into a digital signal, and performs signal processing, and a monitor 508 that displays an image of signal-processed data. In this electron microscope, the nonlinear signal detection system is mounted on signal processing board 507 and the SNR of the detection signal output from detector 506 is improved.

According to the nonlinear signal detection system of the present invention, it is possible to improve the SNR of the input signal in the wide noise intensity range. Therefore, due to a difference between detectors 506, for example, even though the SNR of the detection signal is greatly dispersed, it is possible to acquire a signal in which the SNR is stably improved. Further, the noise generation circuit or the adding circuit is not required, and therefore it is possible to reduce the apparatus in size, reduce costs, and save power.

Second Embodiment

In the first embodiment, by adjusting the positive feedback gain and the negative feedback gain, the state transition level, the response speed, or the output signal amplitude can be arbitrarily adjusted, and serviceability thereof is shown. In only the positive feedback gain and the negative feedback gain, however, it is impossible to independently adjust the state transition level, the response speed, and the output signal amplitude. Consequently, in a second embodiment, a nonlinear signal detection system is provided that can adjust all the characteristics of the state transition level, the response speed, and the output signal amplitude of the nonlinear characteristic unit.

Figure 2:
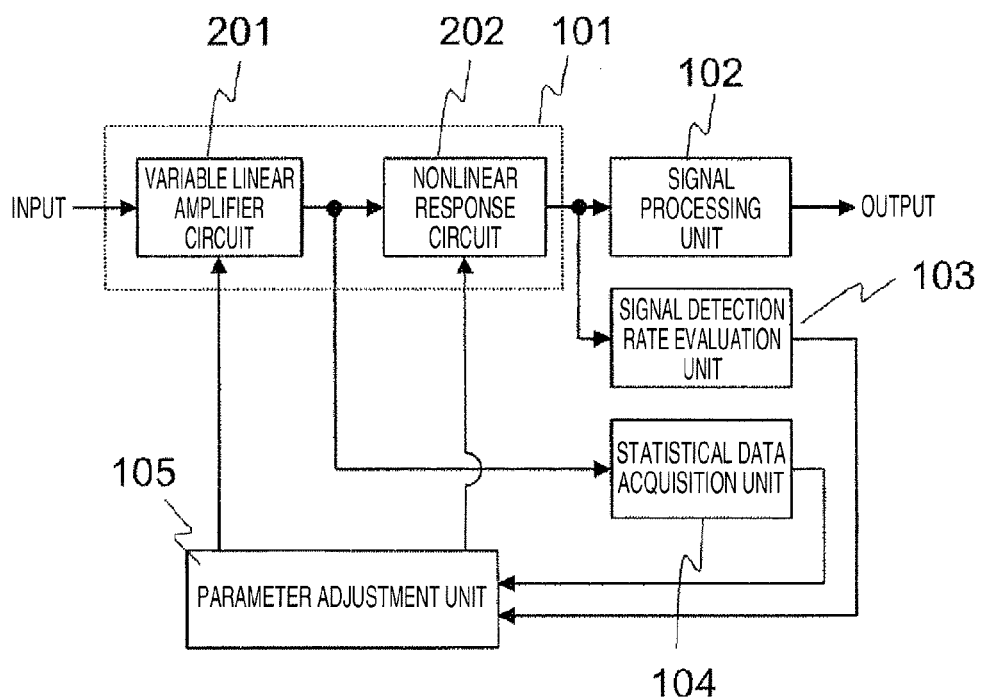
FIG. 2 is a block diagram illustrating a nonlinear signal detection system according to a second embodiment.

FIG. 2 is a diagram illustrating a configuration of the nonlinear signal detection system according to the second embodiment. The nonlinear signal detection system of the present invention is configured by statistical data acquisition unit 104 that measures an average value or distribution of an input signal in which noise is superimposed on a desired signal, calculates amplitude of the desired signal, noise dispersion, and the like, and outputs obtained calculation data, nonlinear characteristic unit 101 that responds nonlinearly to the amplitude of voltage or current of the input signal and outputs a signal, signal detection ratio evaluation unit 103 that evaluates a detection ratio of the desired signal in an output signal from nonlinear characteristic unit 101 and outputs detection ratio data, parameter adjustment unit 105 that adjusts control parameter of nonlinear characteristic unit 101 based on the detection ratio data and the calculation data obtained by statistical data acquisition unit 104, and signal processing unit 102 that performs signal processing of the output signal from nonlinear characteristic unit 101 and conversion to digital data or image data.

Further, nonlinear characteristic unit 101 is characterized in that it is configured by variable linear amplifier circuit 201 that can linearly amplify an input signal and adjust a gain, and nonlinear response circuit 202 that responds nonlinearly to the amplitude of voltage or current of the linearly-amplified input signal. Further, parameter adjustment unit 105 is characterized in that it adjusts one gain of variable linear amplifier circuit 201 and another gain of nonlinear response circuit 202.

Figure 10A:
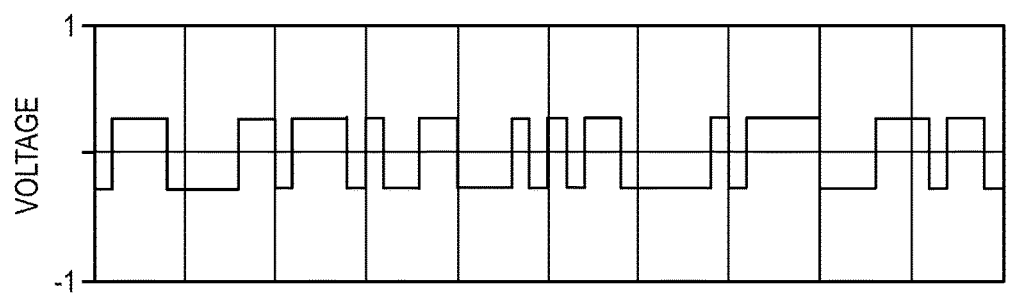
FIGS. 10A-10C are diagrams illustrating input-output waveforms of the nonlinear signal detection system in the case in which the noise intensity is weak.
Figure 10B:
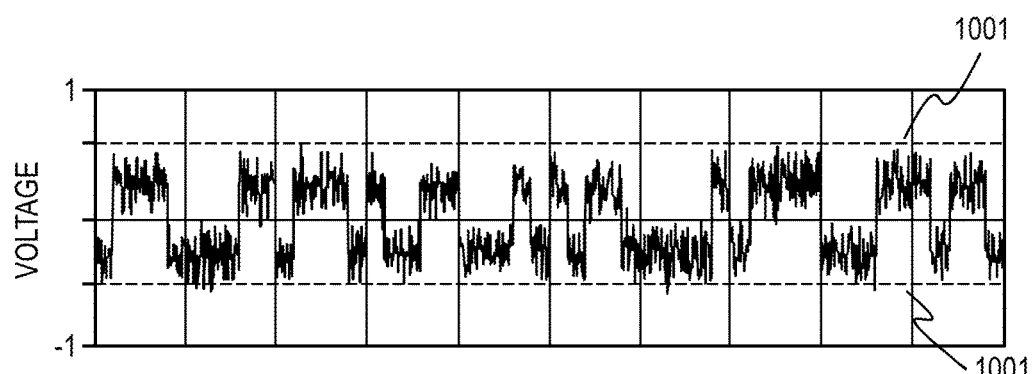
Figure 10C:
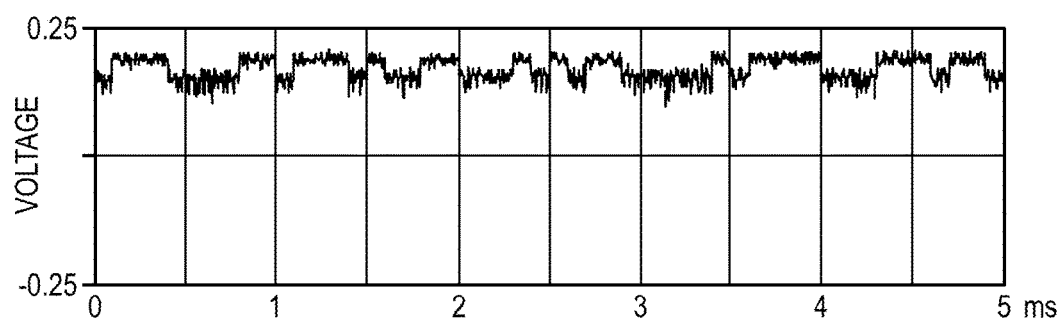
Figure 11A:
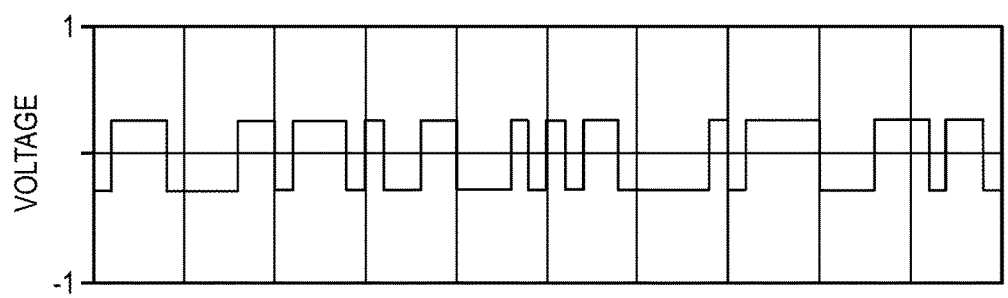
FIGS. 11A-11C are diagrams illustrating the input-output waveforms of the nonlinear signal detection system in the case in which the noise intensity is appropriate.
Figure 11B:
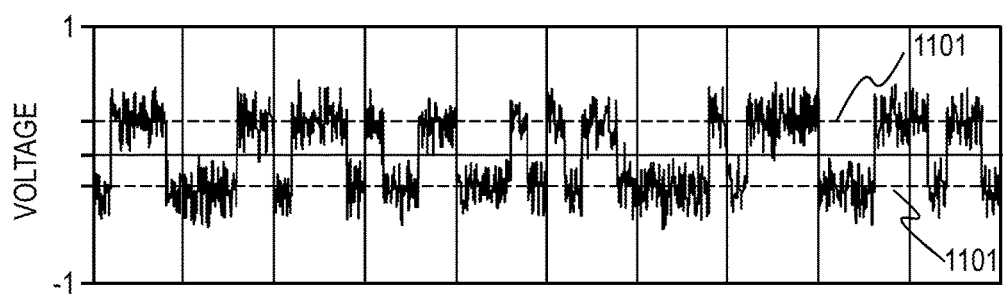
Figure 11C:
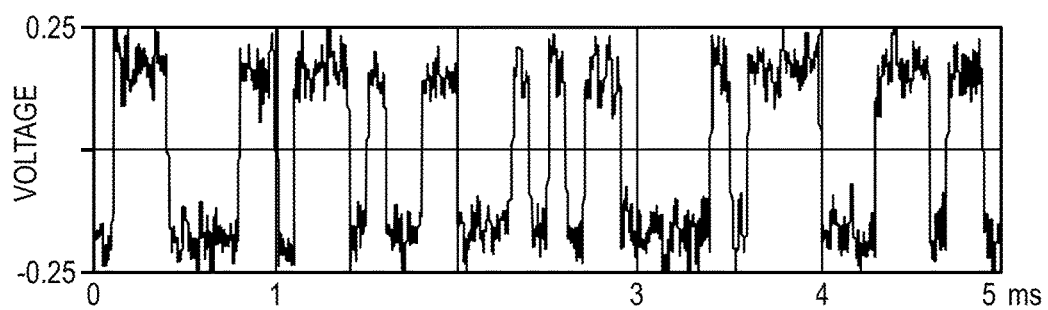
Figure 12A:
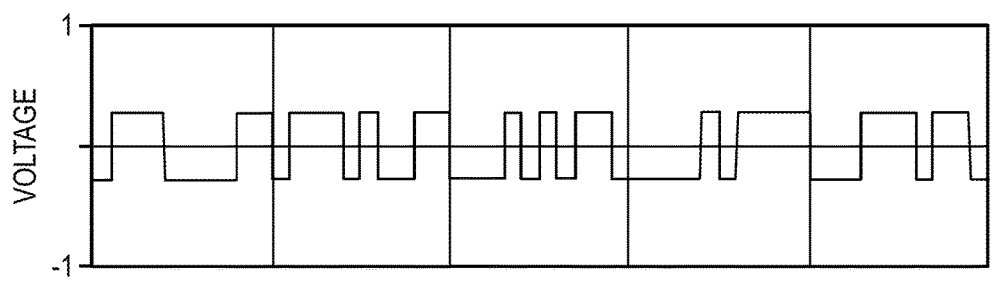
FIGS. 12A-12C are diagrams illustrating the input-output waveforms of a nonlinear response circuit in the nonlinear signal detection system of the second embodiment.
Figure 12B:
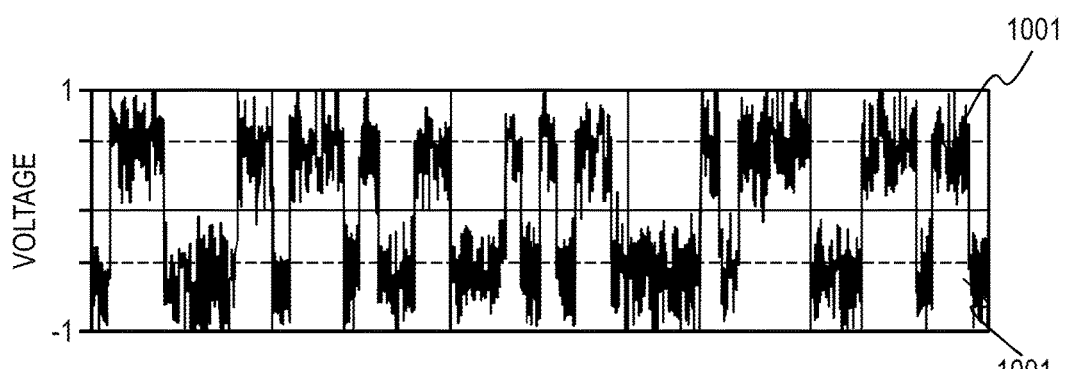
Figure 12C:
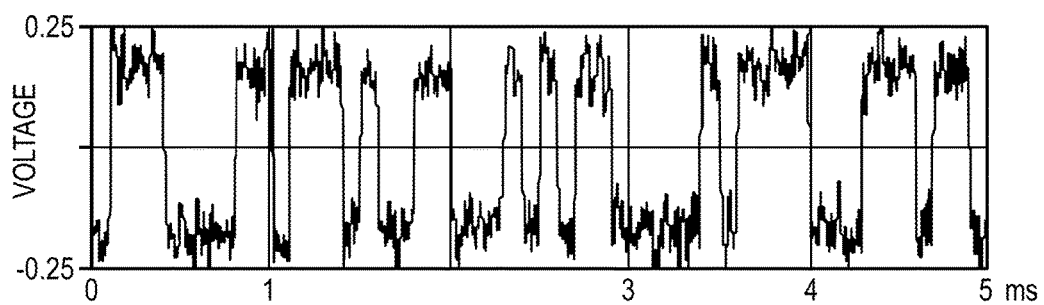

Here, effects of variable linear amplifier circuit 201 will be described with reference to FIGS. 10, 11, and 12. FIG. 10 illustrates a state in which noise intensity is weak, an input signal (b) is not larger than state transition level 1001, and a desired signal (a) is undetectable in an output signal (c). FIG. 11 illustrates a waveform in the case in which a parameter of nonlinear response circuit 202 is adjusted to reduce the state transition level and the input signal (b) is larger than state transition level 1101, and the desired signal (a) is detectable in the output signal (c) with high accuracy. FIG. 12 illustrates a waveform in the case in which a value of the state transition level is the same as that illustrated in FIG. 10 and further a linear gain of variable linear amplifier circuit 201 is increased, and the desired signal (a) is detectable in the output signal (c) with high accuracy in the same manner as in the case in which the state transition level is reduced.

That is, variable linear amplifier circuit 201 has the same effect as that of the adjustment of the state transition level, and on the other hand, fails to exert an influence on the response speed and the output signal amplitude. A relationship illustrated in [MATH. 5] holds between the linear gain c, the positive feedback gain a, and the negative feedback gain b of variable linear amplifier circuit 201 and the response speed, the output signal amplitude, and the state transition level. Therefore, the response speed is adjusted by the positive feedback gain a, the output signal amplitude is then adjusted by the negative feedback gain b, and the state transition voltage is further adjusted by the linear gain c. As a result, the state transition level, the response speed, and the output signal amplitude are adjustable to arbitrary values.

In addition, a detailed adjustment method for adjusting the state transition level, the response speed, and the output signal amplitude of nonlinear characteristic unit 101 will be described later.

$$\text{response speed} \propto 1/a$$

$$\text{output signal amplitude} \propto a^{1/2}, b^{-3/2}$$

$$\text{state transition voltage} \propto a^{3/2}, b^{-3/2}, c \qquad [\text{MATH. 5}]$$

Figure 13:
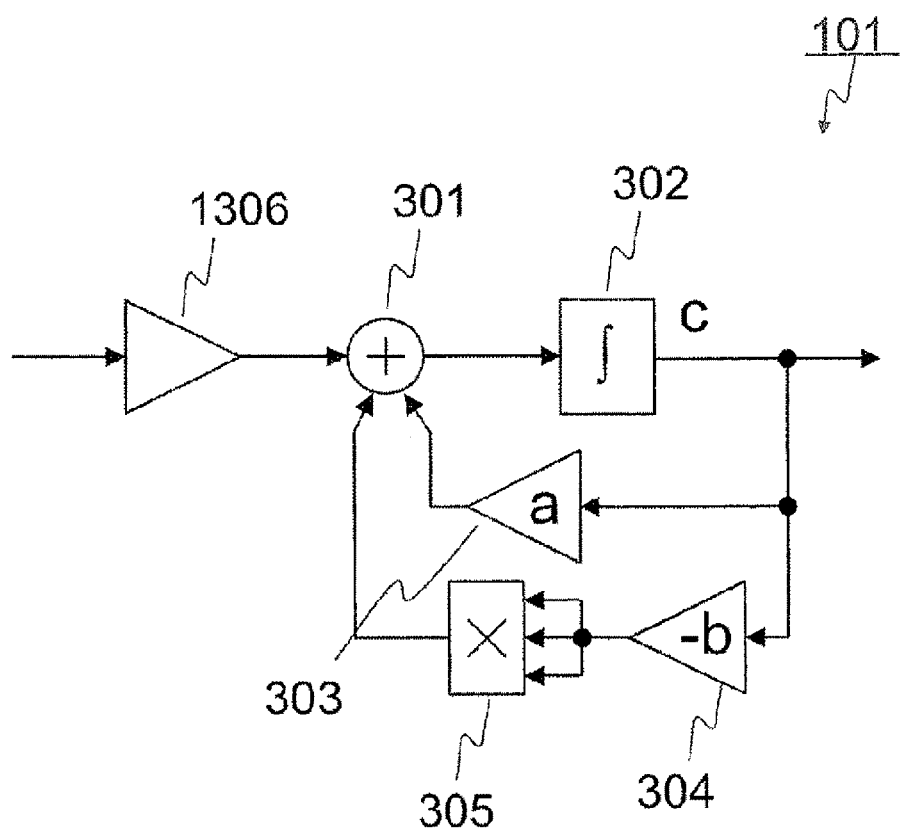
FIG. 13 is a diagram illustrating an example of the nonlinear characteristic unit in the nonlinear signal detection system of the second embodiment.

An example of a configuration of the nonlinear characteristic unit in the nonlinear signal detection system described in the present embodiment is illustrated in FIG. 13. Nonlinear characteristic unit 101 is configured by a variable linear amplifier circuit 1306 that linearly amplifies the input signal, adding circuit 301 that adds to the linearly-amplified signal two feedback signals from positive feedback amplifier circuit 303 and cube circuit 305, integral circuit 302 that integrates the added signal, positive feedback amplifier circuit 303 that linearly amplifies the integrated signal and outputs it to adding circuit 301, negative feedback amplifier circuit 304 that linearly amplifies the integrated signal and outputs it to cube circuit 305, and cube circuit 305 that outputs to adding circuit 301 a signal in which the linearly amplified signal is cubed.

Figure 7:
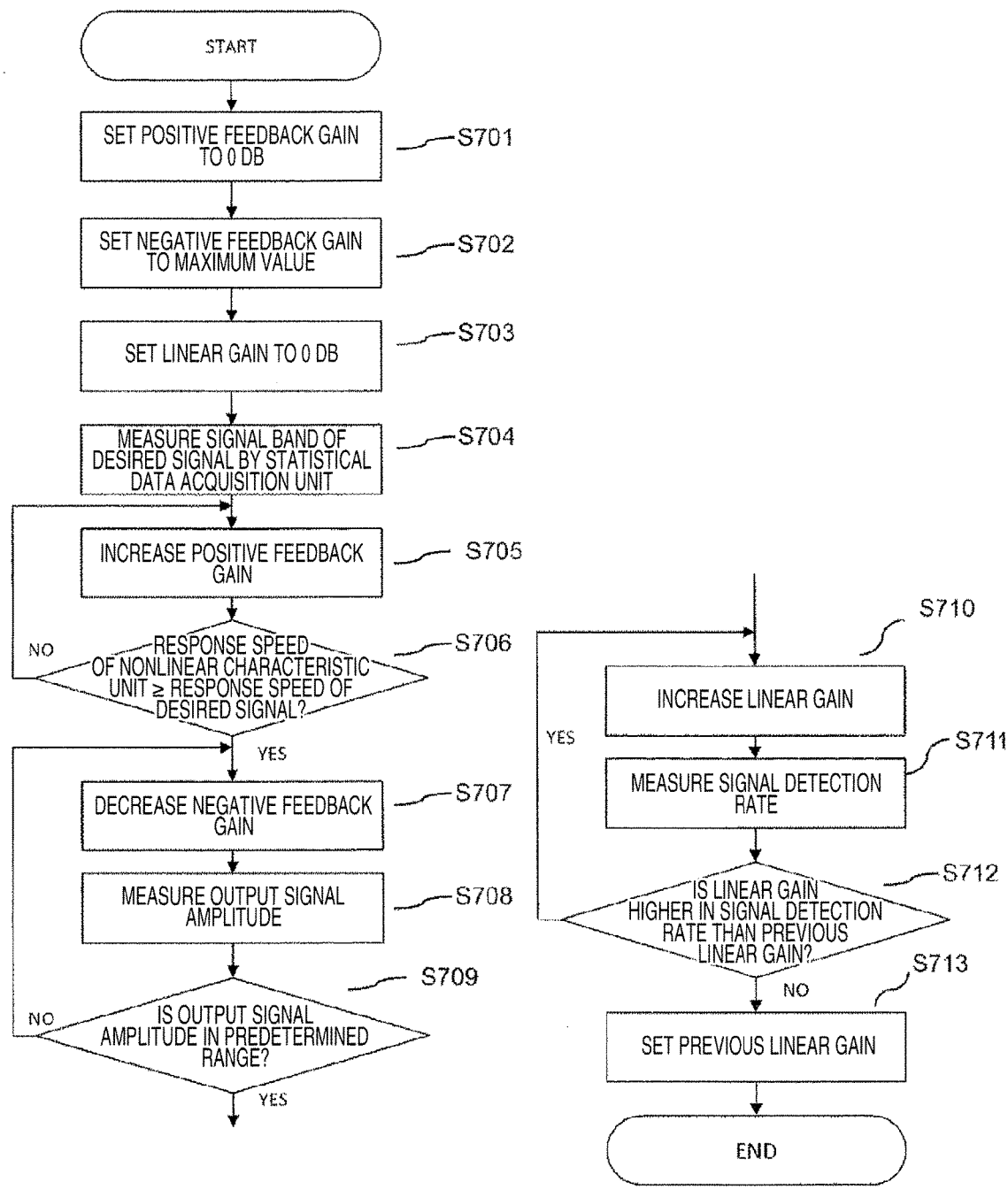
FIG. 7 is a diagram illustrating an example of a flowchart for adjusting a control parameter of the second embodiment.

In the present embodiment, the adjustment sequence for adjusting the state transition level, the response speed, and the output signal amplitude of nonlinear characteristic unit 101 is illustrated in FIG. 7. When the adjustment sequence is started, the positive feedback gain is first set to 0 dB (S701), the negative feedback gain is set to a maximum value (S702), and the linear gain is set to 0 dB (S703). As described previously, the reason is that there is a possibility that in the case in which the positive feedback gain is high, whole nonlinear characteristic unit 101 switches to a positive feedback operation and the operation becomes unstable. If a stable operation is guaranteed, an initial value is not limited to the above value.

Next, a signal band of the desired signal is measured by statistical data acquisition unit 104 (S704). Next, in order that a band of nonlinear characteristic unit 101 may be made to be higher than that of the desired signal, the positive feedback gain is increased and the band of the nonlinear characteristic unit is evaluated (S705). Further, if the band of the nonlinear characteristic unit is higher than that of the desired signal, the process proceeds to the next step, and if the band of the nonlinear characteristic unit is lower than that of the desired signal, the positive feedback gain is increased again and the band is evaluated (S706).

Next, the negative feedback gain is decreased (S707), and the output signal amplitude is measured (S708). If the output signal amplitude is in a predetermined range, the process proceeds to the next step. If the output signal amplitude is out of the predetermined range, the negative feedback gain is decreased again (S709).

Next, the linear gain of variable linear amplifier circuit 201 is increased (S710), the signal detection ratio is measured (S711), and whether the linear gain is higher in the signal detection ratio than the previous linear gain is evaluated. If the linear gain is higher in the signal detection ratio than the previous linear gain, the linear gain is increased and measured again (S712), and if the linear gain is lower in the signal detection ratio than the previous linear gain, the previous linear gain is set (S713), and the adjustment is completed.

According to the above configuration, the positive feedback gain, the negative feedback gain, and the linear gain of the nonlinear characteristic unit are adjusted, and thereby it is possible to arbitrarily adjust the state transition level, the response speed, and the output signal amplitude that are impossible to arbitrarily adjust in the configuration of the first embodiment.

REFERENCE SIGNS LIST

101 . . . Nonlinear characteristic unit
102 . . . Signal processing unit
103 . . . Signal detection ratio evaluation unit
104 . . . Statistical data acquisition unit
105 . . . Parameter adjustment unit
201 . . . Variable linear amplifier circuit
202 . . . Nonlinear response circuit
301 . . . Adding circuit
302 . . . Integral circuit
303 . . . Positive feedback amplifier circuit
304 . . . Negative feedback amplifier circuit
305 . . . Cube circuit
306 . . . Linear amplifier circuit
307 . . . Nonlinear response circuit
401-405 . . . Operational amplifier
406, 407 . . . Multiplication circuit
408-416 . . . Resistance
417 . . . Capacitor
418, 419 . . . Variable resistance
501 . . . Electron gun
502-1, 502-2 . . . Lens
503 . . . Deflection electrode
504 . . . Stage
505 . . . Sample
506 . . . Detector
507 . . . Signal processing board
508 . . . Monitor
1001, 1101 . . . State transition level
1306 . . . Linear amplifier circuit

The invention claimed is:

1. A weak signal detection system comprising:
a statistical data acquisition unit that measures an average value or distribution of an input signal in which noise is superimposed on a desired signal, calculates amplitude of the desired signal, noise dispersion, and the like, and outputs obtained calculation data;
a nonlinear characteristic unit that outputs a signal that responds nonlinearly to amplitude of voltage or current of the input signal;
a signal detection ratio evaluation unit that determines whether an output signal from the nonlinear characteristic unit is the desired signal, calculates a detection ratio assuming the output signal is the desired signal, and outputs detection ratio data;
a parameter adjustment unit that adjusts a control parameter pertaining to responsiveness of the nonlinear characteristic unit based on the detection ratio data obtained by the signal detection ratio evaluation unit and the calculation data obtained by the statistical data acquisition unit; and
a signal processing unit that performs signal processing of the output signal from the nonlinear characteristic unit and converts the signal-processed output signal into digital data or image data.

2. The weak signal detection system according to claim 1, wherein the nonlinear characteristic unit includes a linear amplifier circuit that linearly amplifies an input signal and a nonlinear response circuit that responds nonlinearly to the input signal, adjusts a gain of the nonlinear response circuit by the parameter adjustment unit, and adjusts a state transition level, a response speed, and output signal amplitude that respond to voltage of the input signal in the nonlinear characteristic unit.

3. The weak signal detection system according to claim 2, wherein the nonlinear response circuit of the nonlinear characteristic unit includes:
an adding circuit that adds a plurality of input signals and outputs the added input signal;
an integral circuit that integrates the output signal from the adding circuit;
a positive feedback amplifier circuit that linearly amplifies the signal integrated by the integral circuit and outputs the linearly-amplified signal to the adding circuit;
a negative feedback amplifier circuit that linearly amplifies the signal integrated by the integral circuit and outputs the linearly-amplified signal; and
a cube circuit that outputs to the adding circuit a signal obtained by cubing the output signal from the negative feedback amplifier circuit, wherein
a gain of the positive feedback amplifier circuit and a gain of the negative feedback amplifier circuit are adjusted by the parameter adjustment unit.

4. The weak signal detection system according to claim 2, wherein the nonlinear characteristic unit includes a variable linear amplifier circuit that can linearly amplify the input signal and adjust the gain, adjusts the gain of the variable linear amplifier circuit and the gain of the nonlinear response circuit by the parameter adjustment unit, and adjusts the state transition level that responds to the voltage of the input signal in the nonlinear characteristic unit.

5. An electron microscope comprising the weak signal detection system according to claim 1.

* * * * *